United States Patent
Bierman et al.

(10) Patent No.: US 8,052,652 B2
(45) Date of Patent: Nov. 8, 2011

(54) SECUREMENT DEVICE

(75) Inventors: Steven F. Bierman, Del Mar, CA (US);
Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

(21) Appl. No.: 12/480,583

(22) Filed: Jun. 8, 2009

(65) Prior Publication Data
US 2010/0022962 A1    Jan. 28, 2010

Related U.S. Application Data

(60) Provisional application No. 61/083,079, filed on Jul. 23, 2008.

(51) Int. Cl.
*A61M 5/32* (2006.01)
(52) U.S. Cl. .................. 604/177; 604/174; 604/180
(58) Field of Classification Search .......... 604/178–180, 604/174, 177
See application file for complete search history.

(56) References Cited

U.S. PATENT DOCUMENTS

| | | | |
|---|---|---|---|
| 2,707,953 A | 7/1952 | Ryan | |
| 3,046,984 A | 7/1962 | Eby | |
| 3,059,645 A | 10/1962 | Hasbrouck et al. | |
| 3,556,096 A | 1/1971 | Fuller et al. | |
| 3,677,250 A | 7/1972 | Thomas | |
| 3,973,656 A | 8/1976 | Zumbro | |
| 4,020,835 A | 5/1977 | Nordstrom et al. | |
| 4,057,066 A * | 11/1977 | Taylor | 604/180 |
| 4,059,105 A | 11/1977 | Cutruzzula et al. | |
| 4,113,307 A | 9/1978 | Day | |
| 4,133,307 A | 1/1979 | Ness | |
| 4,142,527 A | 3/1979 | Garcia | |
| 4,449,975 A | 5/1984 | Perry | |
| 4,453,933 A | 6/1984 | Speaker | |
| 4,516,293 A | 5/1985 | Beran | |
| 4,633,863 A | 1/1987 | Filips et al. | |
| 4,650,473 A | 3/1987 | Bartholomew et al. | |
| 4,711,636 A | 12/1987 | Bierman | |
| 4,778,446 A | 10/1988 | Jensen | |
| 4,919,654 A | 4/1990 | Kalt | |
| 4,950,285 A | 8/1990 | Wilk | |
| 4,966,590 A | 10/1990 | Kalt | |
| 5,000,741 A | 3/1991 | Kalt | |
| 5,037,397 A | 8/1991 | Kalt et al. | |
| 5,073,170 A | 12/1991 | Schneider | |
| 5,079,804 A | 1/1992 | Gregurich et al. | |
| 5,098,399 A | 3/1992 | Tollini | |
| 5,123,913 A | 6/1992 | Wilk et al. | |
| 5,147,322 A | 9/1992 | Bowen et al. | |
| 5,188,609 A | 2/1993 | Bayless et al. | |
| 5,192,273 A | 3/1993 | Bierman | |
| 5,192,274 A | 3/1993 | Bierman | |
| 5,195,981 A | 3/1993 | Johnson | |

(Continued)

*Primary Examiner* — Kevin C Sirmons
*Assistant Examiner* — Brandy C Scott
(74) *Attorney, Agent, or Firm* — Knobbe, Martens, Olson & Bear LLP

(57) ABSTRACT

A securement device includes a filament which passes underneath at least a portion of the securement device and can be secured about a medical article to be retained. The filament may be secured about the medical article without the use of adhesive. At least a portion of the securement device underlying the medical article may comprise a compressible material which may be used to exert a restoring force upon the medical article to hold the medical article tightly in place.

28 Claims, 11 Drawing Sheets

U.S. PATENT DOCUMENTS

| | | |
|---|---|---|
| 5,224,935 A | 7/1993 | Hollands |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,314,411 A | 5/1994 | Bierman et al. |
| 5,342,317 A | 8/1994 | Claywell |
| 5,354,282 A | 10/1994 | Bierman |
| 5,395,344 A | 3/1995 | Beisang et al. |
| 5,413,562 A | 5/1995 | Swauger |
| 5,443,460 A | 8/1995 | Miklusek |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,496,282 A | 3/1996 | Militzer et al. |
| 5,520,656 A | 5/1996 | Byrd |
| 5,522,803 A | 6/1996 | Teissen-Simmony |
| 5,527,293 A | 6/1996 | Zamierowski |
| 5,637,098 A | 6/1997 | Bierman |
| 5,643,216 A | 7/1997 | White |
| D393,903 S | 4/1998 | Bierman |
| 5,792,115 A | 8/1998 | Horn |
| 5,855,591 A | 1/1999 | Bierman |
| 6,117,163 A * | 9/2000 | Bierman ...................... 606/232 |
| 6,213,979 B1 | 4/2001 | Bierman |
| 6,582,403 B1 | 6/2003 | Bierman et al. |
| 7,024,827 B2 | 4/2006 | Gregory et al. |
| 7,204,827 B2 | 4/2007 | Kessler |

\* cited by examiner

SECUREMENT DEVICE

CROSS-REFERENCE TO RELATED APPLICATIONS

This application claims the benefit under 35 U.S.C. §119 (e) of U.S. Provisional Application No. 61/083,079, filed Jul. 23, 2008, which is hereby expressly incorporated by reference in its entirety.

BACKGROUND

1. Field

The present invention relates in general to a medical article securement device and more particularly, to anchoring devices for anchoring or securing medical articles relative to the body of a patient. In one mode, the present invention involves a medical article securement system that secures a medical article in place through the use of a filament.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical article properly positioned for the duration of treatment, the catheter or medical article can be secured to the patient in a variety of ways. Most commonly, this involves taping or suturing the catheter or medical article to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin. Such repeated applications of tape over the catheter or medical article can additionally lead to the build up of adhesive residue on the outer surface of the catheter or medical article. This residue can result in contaminants adhering to the medical article itself, increasing the likelihood of infection of the insertion site. This residue can also make the catheter or medical article stickier and more difficult to handle for healthcare providers.

Suturing also carries risk, both to healthcare workers and patients. Healthcare workers can suffer accidental needle-stick injury, which may expose them to hepatitis, HIV, and other pathogens. Patients can suffer local or even systemic infection from suture, as well as scarring and pain.

SUMMARY

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

One aspect of the present invention is a device for securing a medical article to the body of a patient. The device comprises an adhesive layer configured to contact the skin of a patient and a structural layer overlying the adhesive layer. The structural layer includes at least one aperture extending therethrough and a receiving space. The device further includes a filament extending underneath a portion of the structural layer and through the aperture. The filament is configured to be secured about a medical article to retain the medical article against the receiving space.

Another aspect is a securement device for retaining a medical article therein. The device includes a base portion configured to be secured to the skin of a patient and a filament extending underneath at least a receiving portion of the base portion. The receiving portion is configured to contact the medical article retained therein includes a compressible material.

Another aspect is a device for securing a medical article in place. The device includes an adhesive layer, a structural layer overlying the adhesive layer, and at least two apertures extending through the structural layer. A portion of the structural layer located between the at least two apertures includes a compressible material. At least a portion of the structural layer located adjacent the at least two apertures includes a tear-resistant material. The device further includes a filament extending underneath at least a portion of the structural layer and between the at least two apertures. The filament is configured to be secured about the medical article without the use of adhesive.

Another aspect is an anchoring system for securing a portion of a medical article to a body of a patient that includes an anchor having two apertures and a receiving space therebetween. The two apertures are spaced from each other so as to receive at least a portion of the medical article on the receiving space. The system further includes at least one filament that passes through the two apertures and has two ends. The filament includes a first set of protuberances positioned between the ends of the filament. At least a portion of the filament is sized and shaped to pass through the two apertures. Each protuberance is sized and shaped to inhibit movement of the filament through one of the apertures in a first direction.

DETAILED DESCRIPTION OF THE PREFERRED EMBODIMENTS

The embodiments of the medical article retention system are disclosed in the context of the securement of a medical article, and in particular the securement of a catheter hub utilizing a filament. However, the following description and the accompanying figures, which describe and show the preferred embodiments, are made to demonstrate several possible configurations that a securement system can take to include various aspects and features of the invention. The illustrated embodiments are shown in use with an illustrative example of a catheter hub. The illustration of the securement device in this context is not intended to limit the disclosed aspects and features of the invention to the specified embodiments or to usage only with the illustrated hub. Those of skill in the art will recognize that the disclosed aspects and features of the invention are not limited to any particular embodiment of a securement system, and securement systems, which include one or more of the inventive aspects and features herein described, can be designed for use with a variety of medical articles.

Accordingly, the present retention system also can be successfully utilized in connection with other types of medical articles, such as for example, but without limitation, percutaneous sheath introducers, CVCs, PICCs, Foley catheters, and hemodialyses catheters, surgical drainage tubes, feeding tubes, chest tubes, nasogastric tubes, as well as with electrical wires or cables connected to external or implanted electronic devices or sensors. Thus, as used herein, the term "medical article" is meant generically to include catheters, catheter hubs, fluid supply and drainage lines, connectors, adaptors, electrical wires and cables, and the like, all of which may be retained by the present retention system. It therefore should be understood that the principles of the present invention are not limited to catheter hubs.

Figure 1:
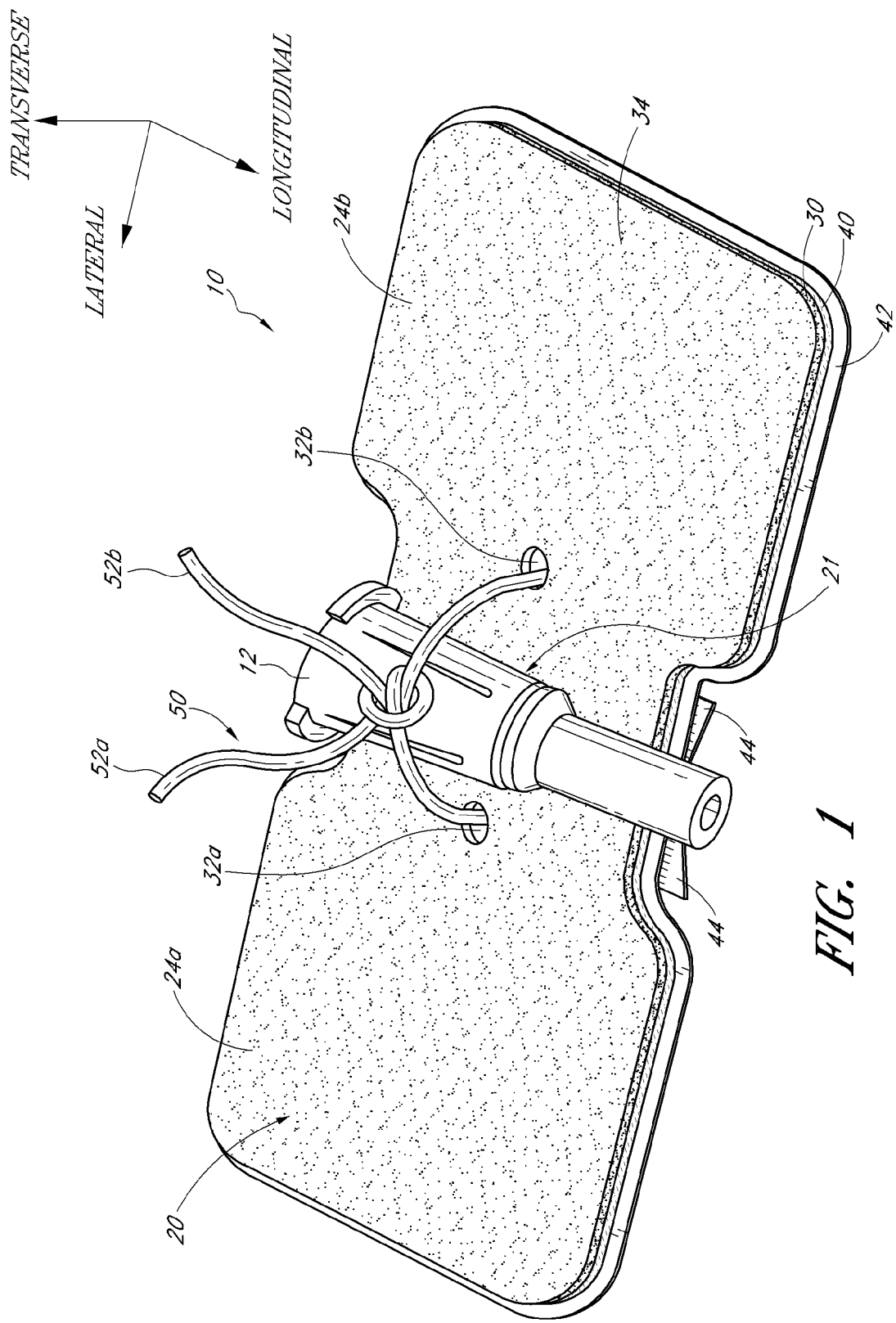
FIG. 1 is a perspective view of a securement device having a medical article retained therein according to a preferred embodiment of the present invention.
Figure 2:
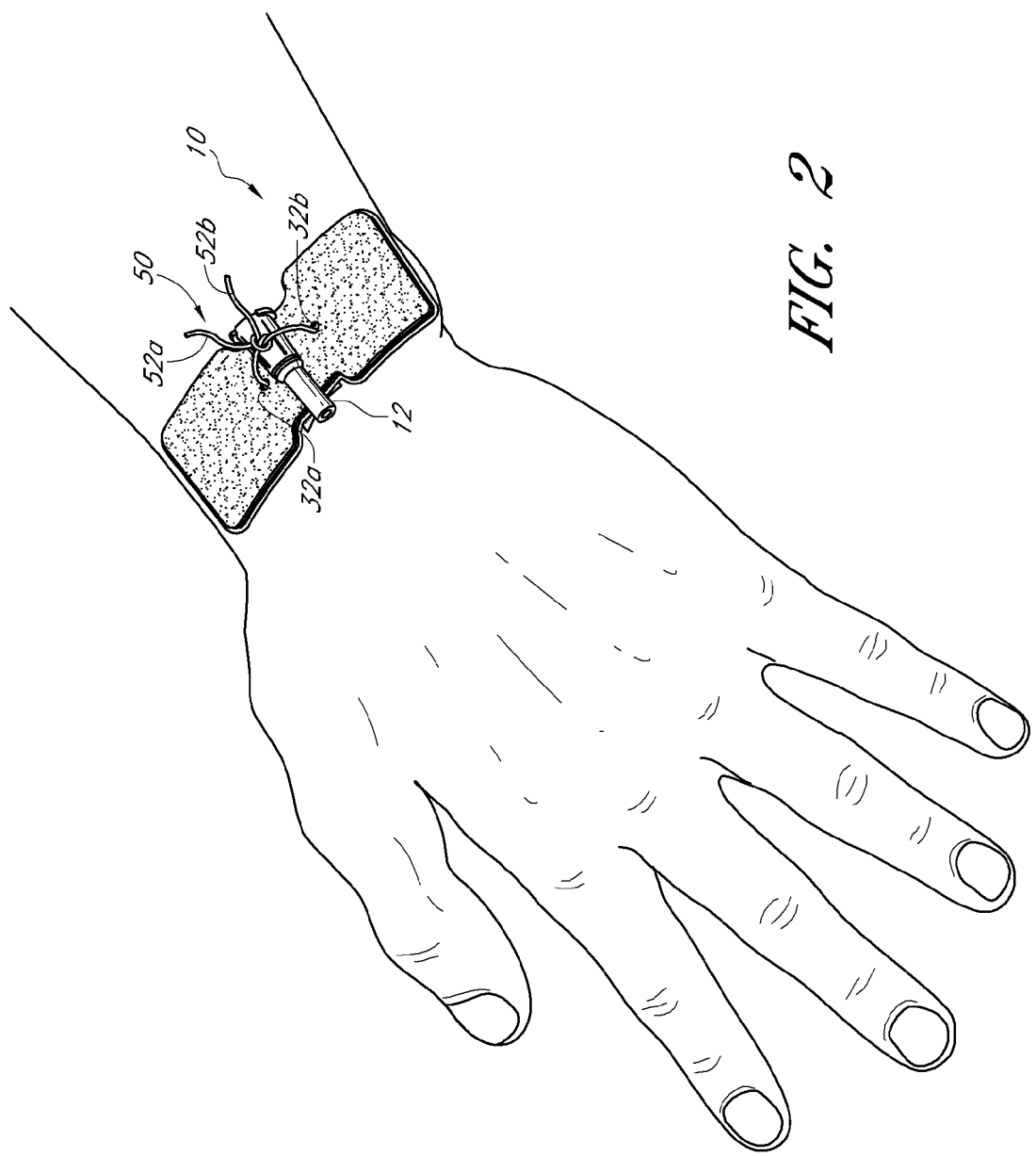
FIG. 2 is a perspective view of the securement device of FIG. 1 disposed on the skin of a patient.

FIG. 1 is a perspective view of an embodiment of a securement device 10 that has a medical article 12 retained therein. FIG. 2 is a perspective view of the securement device 10 from FIG. 1 disposed on the skin of a patient. In the illustrated embodiment the medical article 12 is a catheter hub. As noted above, it is to be understood that, although illustrated with a catheter hub, the securement device 10 herein can be used with other types of medical devices or articles.

The securement device 10 includes an anchor 20 and a retention mechanism 50. The retention mechanism includes at least one filament or thread 50. In the illustrated embodiment the retention mechanism is in the form of a filament 50. The anchor 20 may comprise one or more structural layers 30 and an adhesive layer 40, as will be discussed in greater detail below. The anchor 20 includes a receiving area 21 disposed between opposite ends of the anchor 20. The receiving area 21 is configured to receive a secured portion of the medical article 12.

While the term flexible is used to describe the member 50, only a portion(s) of the member 50 need be flexible. The flexible portion(s) of the member 50 allows the member 50 to be tied together as is illustrated in FIG. 1 so as to secure the medical article 12 in the receiving area 21 of the anchor 20.

The filament 50 may form a unitary structure with the anchor 20 or be separately manufactured and assembled with the anchor 20. The filament 50 interfaces with the anchor 20. In the illustrated embodiments, the filament 50 is separately manufactured and assembled with the anchor 20 via interfaces defined by apertures 32a, 32b. In the illustrated embodiment, the apertures 32a and 32b extend through the structural layer 30 on either side of the receiving area 21. The filament 50 extends through the apertures 32a and 34b, wraps about the medical article 12, and secures to itself. The filament 50 need not secure to itself and may instead secure to a clip, cleat, a cinch, or any other suitable connector. In the illustrated embodiment, the medical article is retained in place by forming a knot using the filament 50.

The securement device 10 and the medical article 12 desirably include interacting coupling structure to couple the medical article 12 to the securement device 10. As will be clear from the disclosure below, the interacting coupling structure that mounts the medical article 12 to the securement device 10 may comprise a variety of structures. An exemplary interacting coupling structure is the filament 50. The terms "mount or secure," when used with reference to the relation between the medical article 12 and the securement device 10, does not necessarily imply that the medical article 12 is immobilized or fixed. Rather, these terms are meant to describe the condition in which the movement of at least a portion of the medical article 12 relative to the securement device 10 is constrained in at least one degree of freedom (e.g., rotational, lateral, longitudinal or transverse).

The securement device 10, and in particular the anchor 20, may be attached at any number of locations on a patient's body. For example, the securement device 10 may be located on the back of a patient's hand or arm 14, as shown in FIG. 2. The securement device 10 may be used to retain medical articles at other locations on the patient's body, e.g., on the radial side of the wrist in connection with catheterization of a radial artery, on the posterior of the patient's torso in connection with epidural catheterization, or on or near the neck to provide access to large vessels such as the jugular vein.

To assist in the description of the components of the securement device 10, and with respect to the FIG. 1, the following coordinate terms are used. A "longitudinal axis" is generally parallel to the plane of anchor 20 and is overlaid by the central axis of the medical article 12 as depicted in FIG. 1. A "lateral axis" is normal to the longitudinal axis and is generally parallel to the plane of the anchor 20, and is parallel to a line extending between apertures 32a and 32b as depicted in FIG. 1. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "top", "bottom", "upper", and "lower" are used in the context of the orientation of the anchoring system illustrated in FIG. 1, and are not intended to imply a limitation to the orientation that the modular catheterization system 10 can assume on the patient.

Anchor

Figure 3:
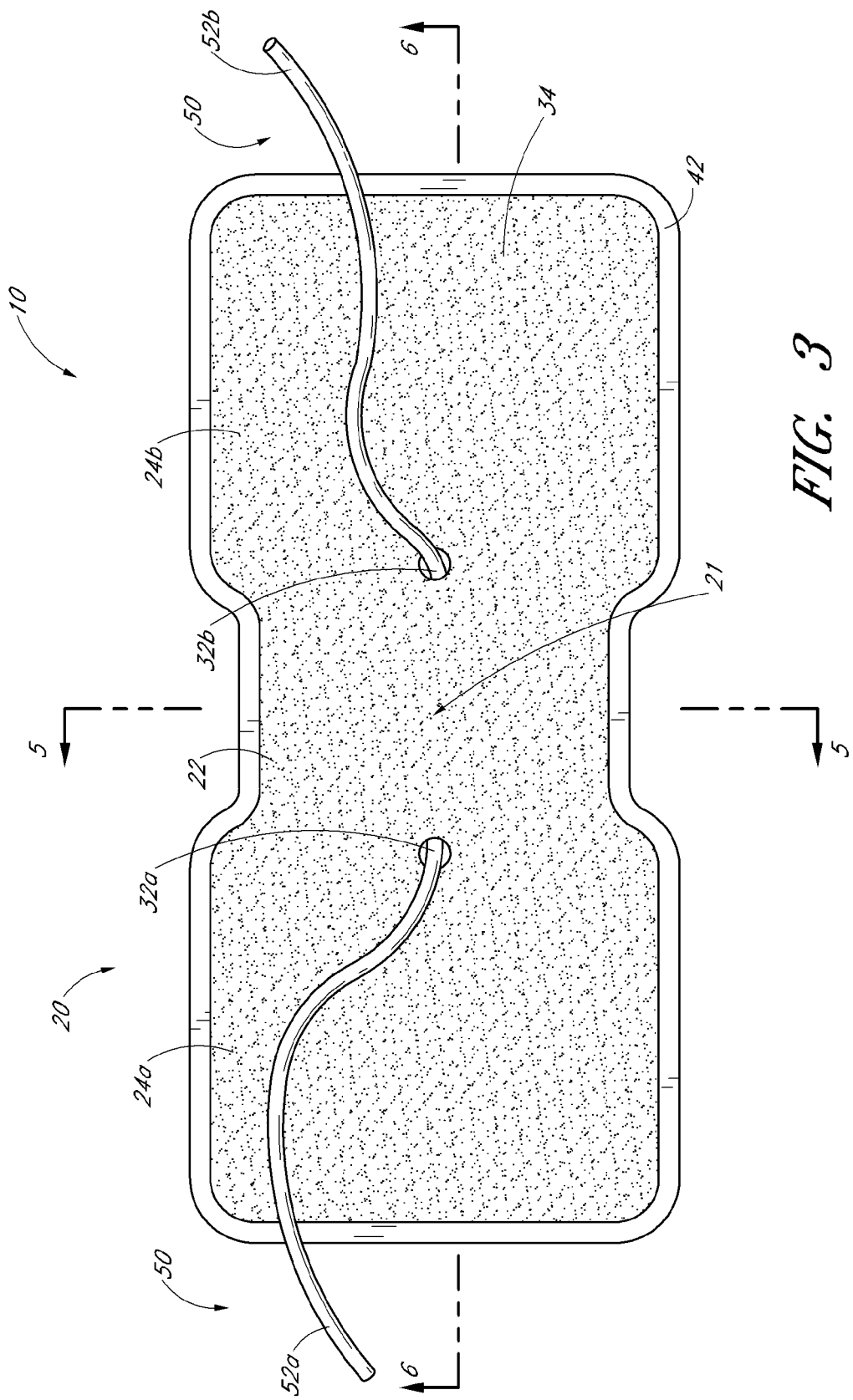
FIG. 3 is a top plan view of the securement device of FIG. 1 without a retained medical article.

FIG. 3 illustrates a top plan view of the securement device 10 without the medical device 12 in place, such that an upper surface 34 of the structural layer 30 of the anchor 20 can be seen. The upper surface 34 of the structural layer faces away from the skin of the patient with the receiving area 21 supporting the medical device 12 to be retained (see FIG. 2).

Figure 4:
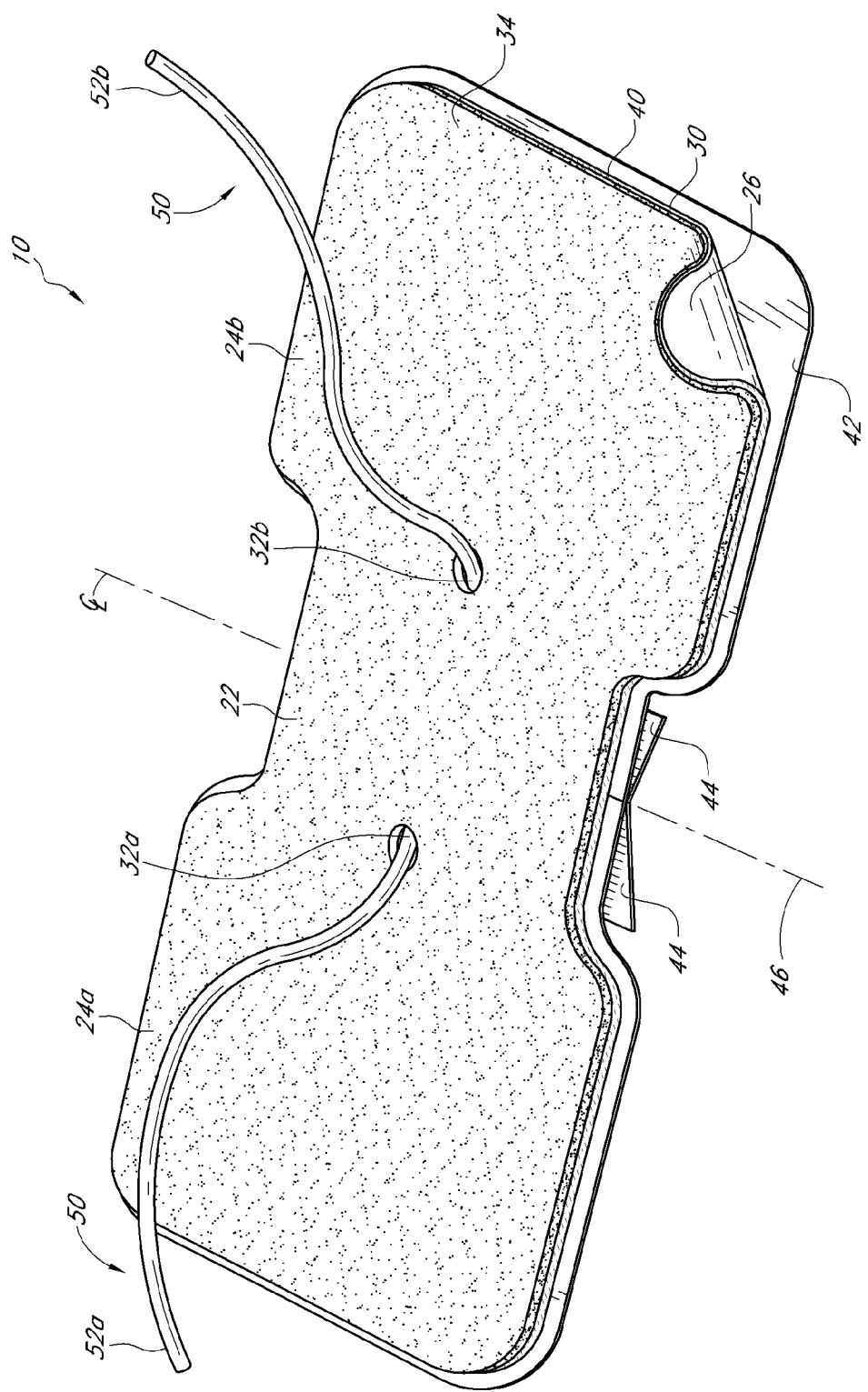
FIG. 4 is a perspective view of the securement device of FIG. 3 showing a liner partially separated from the anchor.
Figure 5:
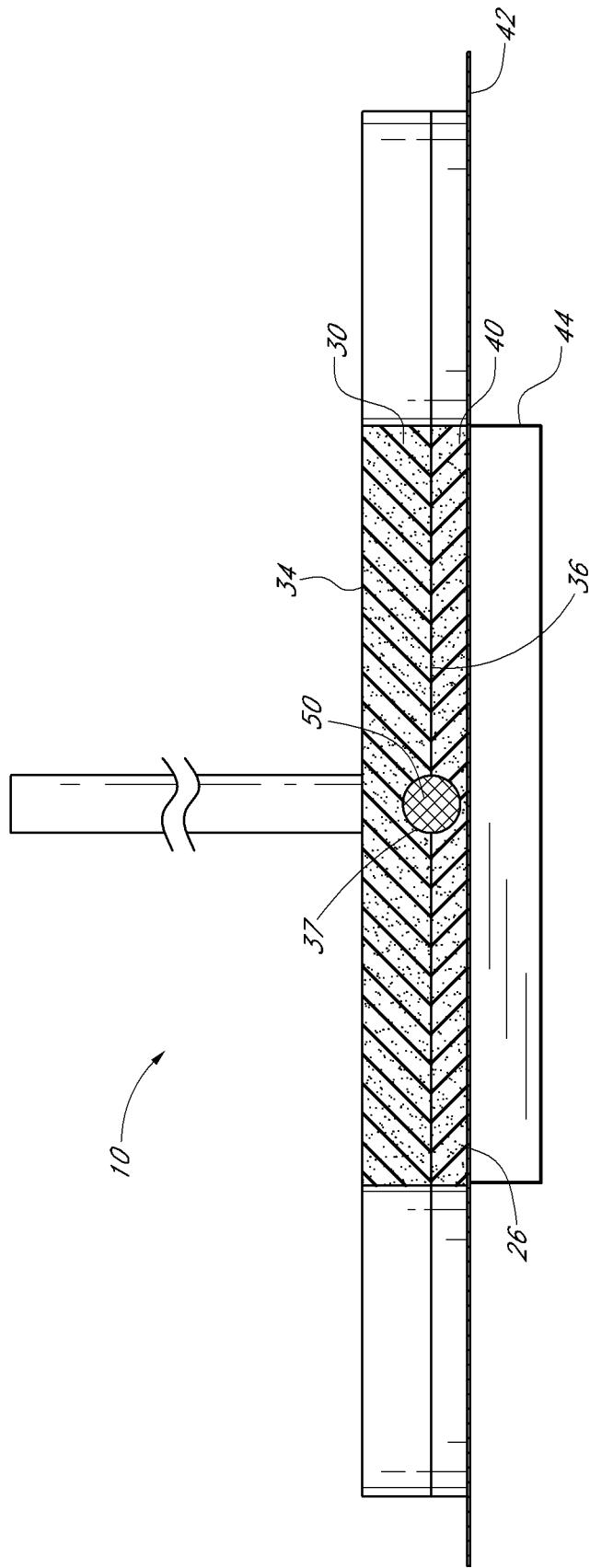
FIG. 5 is a cross sectional view of the securement device of FIG. 3 taken along line 5-5.

FIG. 4 is a perspective view of the securement device 10 of FIG. 3 showing a release liner 42 partially separated from the adhesive layer 40 of the anchor 20. FIG. 5 is a cross sectional view of the securement device of FIG. 3 taken along line 5-5. A lower surface 36 of the structural layer 30 faces towards the skin of the patient, as can be seen in FIG. 5. The adhesive layer 40 is suitable for attaching the anchor 20 to the skin of the patient and covers at least a portion of the lower surface 36 of the structural layer 30. In the illustrated embodiment the adhesive layer 40 extends underneath substantially all of the lower surface 36.

In the illustrated embodiment, the anchor 20 comprises a butterfly configuration. The receiving area 21 is disposed in a central portion 22 of the anchor 20. The anchor 20 is narrower in the longitudinal direction at the central portion 22 than at two end portions 24a, 24b of the anchor 20. In certain embodiments, the anchor 20 may comprise a shape configured to be secured to a specific portion of a patient's body.

In certain embodiments, the anchor 20 may comprise notches, scallops, or other features to enable the medical article to be placed adjacent an insertion site without interfering with the insertion site. In the illustrated embodiment, the central portion 22 may serve such a purpose so that the wider end portions 24a and 24b may extend further in the longitudinal direction beyond the insertion site, but be laterally spaced away from the insertion site on either side to prevent interference. In other embodiments an indentation or scalloped portion may be more pronounced.

A medical provider may also use a notch or other feature of the anchor 20 to align the securement device 10 with an insertion site or other portion of a patient's body. Although only a single shape of the anchor pad 20 is illustrated in FIG. 3, those of skill in the art will recognize that a variety of shapes can be used and thus the anchor 20 is not limited to the illustrated shape. For example, the anchor 20 may have the shape of a dog bone, fan, or other shape and still fall within the scope of the invention.

FIG. 5 best illustrates the laminate structure of an embodiment of the anchor 20. As can be seen in the cross-section, the anchor 20 desirably comprises a laminate structure with one or more upper plastic, paper or foam layers 30 (e.g., closed-cell polyethylene foam) and a lower adhesive layer 40. The lower adhesive layer 40 constitutes a lower surface 26 of the anchor 20 once the release liner 42 is removed. The adhesive layer 40 desirably is a medical-grade adhesive and can be either diaphoretic or nondiaphoretic, depending upon the particular application. Such foam with an adhesive layer is available commercially from Avery Dennison of Painsville, Ohio. Other manufacturers of suitable material include Scapa Group plc of Greater Manchester, UK, Covalence Specialty Materials Corp. of Princeton, N.J., and Worthen Industries of Nashua, N.H.

In other variations, a hydrocolloid adhesive or zinc oxide-based adhesive can advantageously be used upon the anchor 20 for attaching the anchor 20 to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

The anchor 20 may include an antimicrobial agent for killing or inhibiting the growth of microbes such as bacteria, fungi, or viruses. The antimicrobial agent may be a separate layer of the anchor 20 or a part of an existing layer. For example, the adhesive layer 40 may include an anti-microbial agent.

Figure 10:
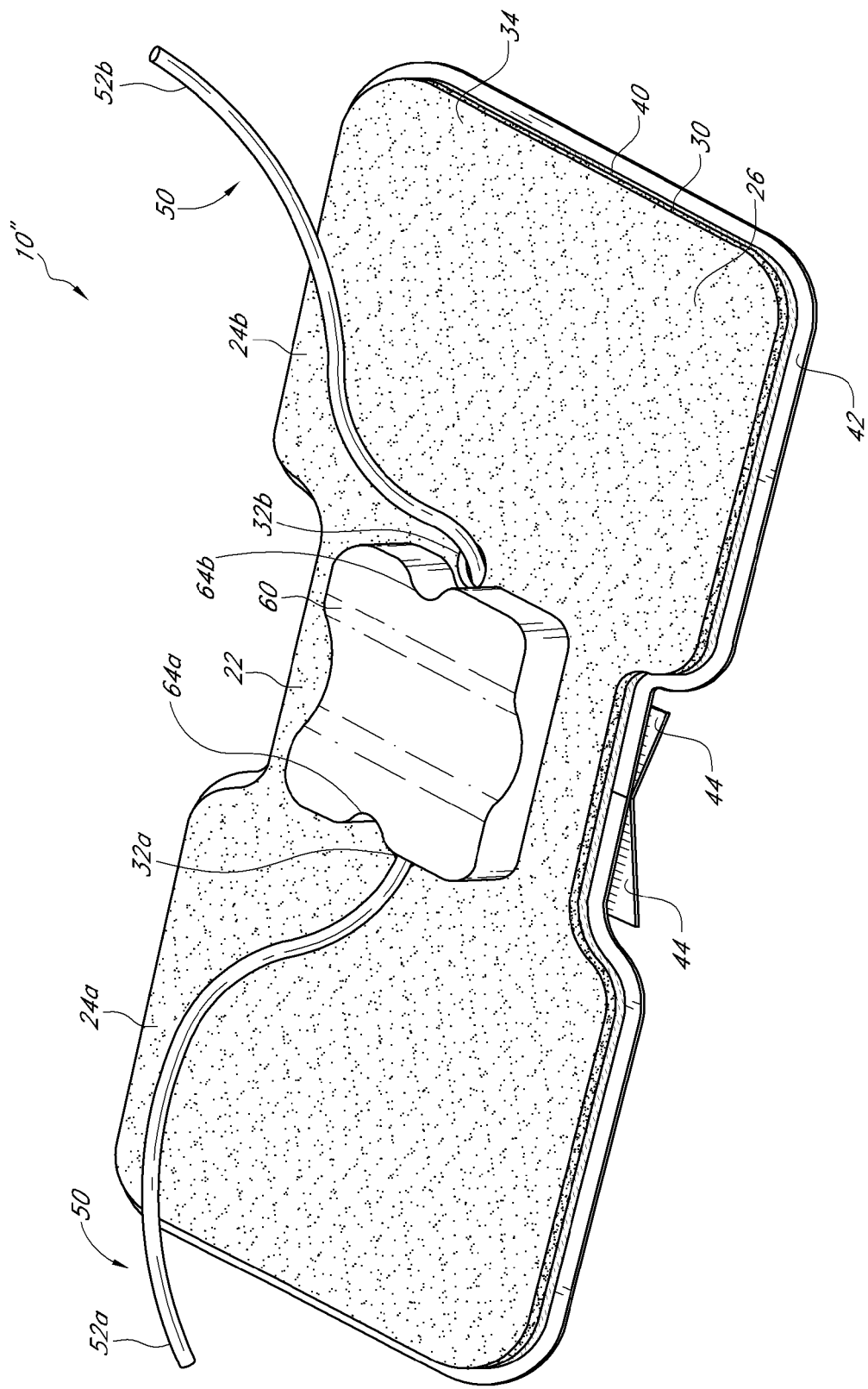
FIG. 10 is a perspective view of an alternate embodiment of a securement device comprising a pedestal on which the medical device may be retained.
Figure 11:
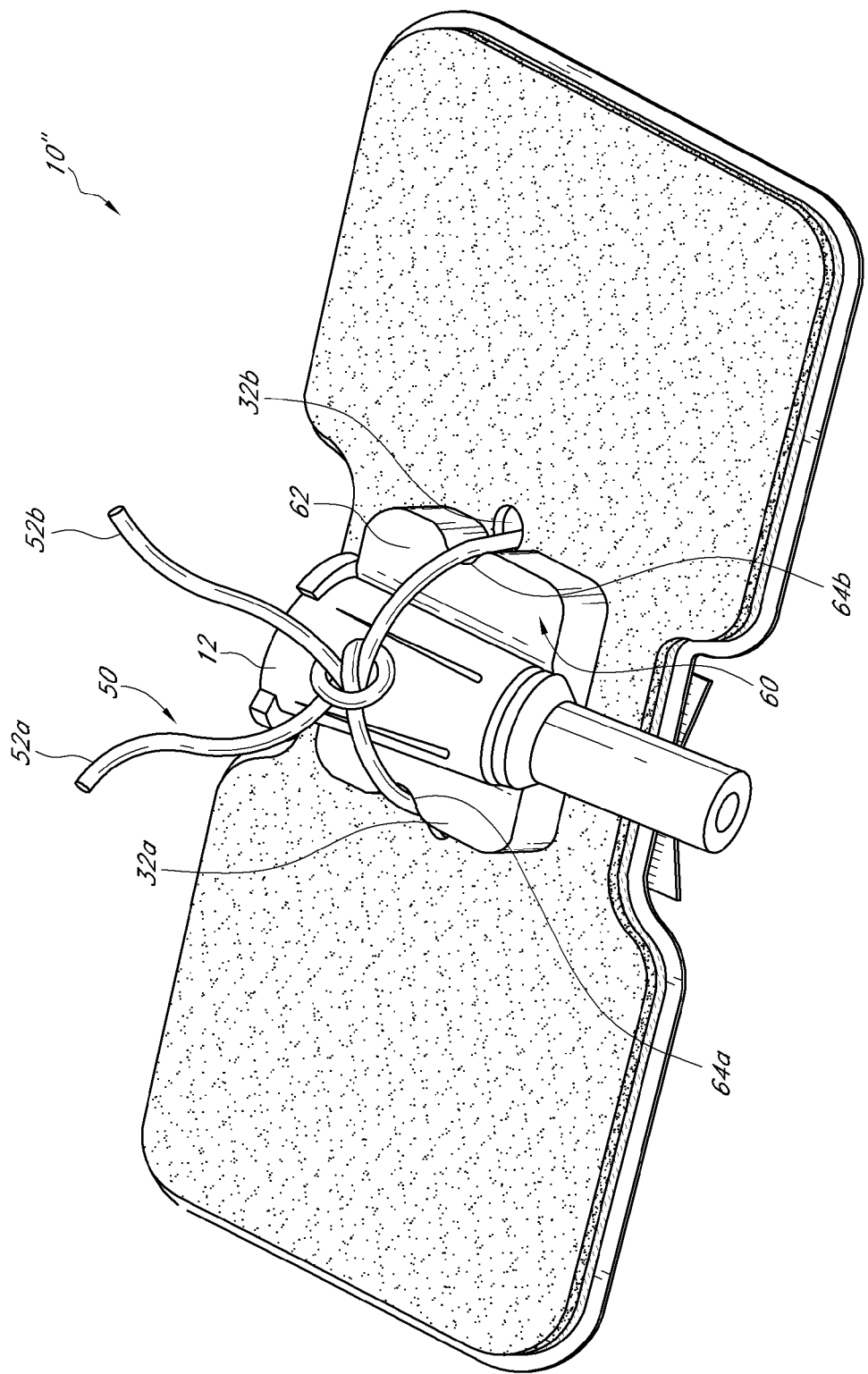
FIG. 11 is a perspective view of the securement device of FIG. 10 having a medical article retained therein.

The upper surface 34 of the structural layer 30 can be roughened, for example, by corona-treating the foam with a low electric charge or by exposing the foam to a chemical primer. The roughened or porous upper surface 34 can improve the quality of an adhesive joint with the bottom surface of any overlying structures such as is illustrated in FIG. 10, or to increase friction between a retained medical article 12 (see FIG. 1) and the upper surface 34 of the structural layer 30. Increased friction inhibits slippage of the secured portion of the medical device 12 relative to the anchor 20.

A removable paper or plastic release liner 42 desirably covers the lower adhesive layer 40 before use. The liner 42 may comprise a polyester or silicone coated liner. The liner 42 preferably resists tearing and desirably is divided into a plurality of pieces to ease attachment of the anchor 20 to a patient's skin. FIG. 4 illustrates partial removal of the liner 42 from the anchor 20. Although as will be described below, the liner 42 in certain embodiments may be removed via pull tabs, rather than by peeling back a corner of the liner 42.

The liner 42 comprises folded over portions to define pull tabs 44. The pull tabs 44 can be utilized to remove the paper or plastic release liner 42 from the lower adhesive layer 40 before use. A healthcare provider uses the pull tab 44 by grasping and pulling on it so that the liner 42 is separated from the lower adhesive layer 40. The pull tabs 44 overcomes any requirement that the healthcare provider pick at a corner edge or other segment of the liner 42 in order to separate the liner 42 from the lower adhesive layer 40.

The pull tabs 44 of course can be designed in a variety of configurations. For example, the pull tabs 44 can be located along a center line of the anchor 20 and oriented so as to face one another, as shown. Alternatively, one or more pull tabs can be located along any line of the anchor 20 in order to ease the application of the anchor 20 onto the patient's skin at a specific site. For example, an area of a patient's skin with an abrupt bend, such as at a joint, can require that the pull tab 44 be aligned toward one of the lateral ends of the anchor 20 rather than along the center line. The pull tabs may extend towards the edge of the anchor 20, as shown, and may extend to the edge of the anchor. In the embodiment illustrated in FIG. 4, the fold forming the pull tabs 44 is located along a centerline 46.

In another variation, the anchor 20 comprises a laminate structure wherein the structural layer 30 comprises an upper woven layer and the lower adhesive layer 40 is on the lower surface 36 of the structural layer 30. The upper layer can be polyester or other suitable polymer or textile materials. One particular suitable material is woven polyester available commercially under the name "Tricot" from Covalence or Worthen. The lower adhesive layer 40 constitutes the lower surface 26 of the anchor 20 after the release liner 42 is removed.

In certain embodiments, at least a portion of the structural layer 30 comprises a tear-resistant material. In one particular embodiment, the structural layer 30 comprises a layer of tear-resistant material. In another embodiment, a portion of tear-resistant material or reinforcing material is utilized to strengthen the interfaces between the filament 50 and the anchor 20. For example, the apertures 32a, 32b from the embodiment illustrated in FIG. 3 can be strengthened by providing a separate layer of tear resistant material around the apertures 32a, 32b and/or incorporating the tear-resistant material in portions of the structural layer 30 that surround the apertures 32a, 32b.

In a particular embodiment, a grommet or similar structure of tear-resistant material may be placed within apertures 32a and 32b. Each grommet may advantageously have a conical or funnel-like shape to help guide the ends 52a, 52b of the filament through the apertures 32a, 32b. The aperture 32a, 32b can taper from a large diameter on a bottom side of the aperture to a smaller diameter on the upper side of the aperture closest to the upper surface 34. In certain embodiments, a filament such as the filament 50 of FIG. 7 may comprise protuberances 54a, 54b. In such an embodiment, the smaller diameter desirably is larger than the maximum diameter of the filament 50 outside of the protuberances 54a, 54b, but smaller than the maximum diameter of the protuberances 54a, 54b.

In another embodiment, the structural layer itself may comprise a laminate structure, wherein a tear resistant layer extends over or under at least a portion of another layer. For example, a tear-resistant layer may be provided in a central region of the structural layer, such that the apertures extend through the tear-resistant layer.

As will be discussed in greater detail below, the tear-resistant nature of the structural layer 30 or portions of the structural layer 30 inhibits tearing or other significant wear in the structural 30 layer caused by the filament 50. The tear-resistant layer may further inhibit the filament 50 from cutting into or through the structural layer 30 and limit undesired movement of the secured medical article.

The resistance of the tear-resistant material to tearing may vary based on the intended use of the securement device 10, as well as the shape, size, and composition of the other components of the securement device 10. For example, a thinner filament 50 or a harder filament 50 may be more likely to cut into the structural layer 30. Similarly, a securement device 10 intended to remain in place for an extended period of time may comprise a more resilient tear-resistant material than one which is intended for shorter-term securement of a medical device, such as a plastic spreader bar.

In addition, the spacing of the apertures 32a and 32b, as well as the size of the component to be retained, will affect the stress on the interior sides of the apertures which the filament 50 rests against. When the medical article 12 is secured in place, the filament 50 may be stretched taut at an angle to the anchor 20. As the angle between the filament 50 and the anchor 20 decreases, the stress on the interior edges of the apertures may increase, and may increase the likelihood of tearing.

The apertures 32a, 32b may be spaced apart along a common lateral axis or offset from each other. The apertures 32a, 32b need not have the same size. In certain embodiments, the apertures 32a and 32b are spaced further apart than the width of the medical article 12 to be retained. Thus, a large distance between apertures 32a and 32b may facilitate retention of a wide range of sizes of medical articles 12, but may increase the acuteness of the angle between the filament 50 and the anchor 20 when the medical article 12 being retained is comparatively small. The use of a strong tear-resistant material may prolong the useful lifetime of such a securement system.

In certain embodiments, at least a portion of the securement device 10 which will underlie a medical article comprises a compressible material. As will be discussed in greater detail below, the compressible portion of the securement device may exert a restoring force upon a medical article retained therein so as to secure the medical article more securely in place.

As noted above with respect to the tear-resistant nature of a portion of the structural layer 30, in certain embodiments, only a portion of the structural layer 30 may comprise a compressible material. In other embodiments, the compressible layer may comprise a laminate structure, wherein a layer of compressible material overlies or underlies an additional layer. In particular embodiments, the compressible portion of the structural layer is located in a portion of the anchor which will underlie a retained medical article, e.g., within receiving area 21.

Filament

The filament 50 includes free ends 52a, 52b. In the embodiment illustrated in FIG. 3, the filament 50 includes at least two protuberances (generally indicated by reference numeral 54a, 54b in FIG. 6) positioned between the ends 52a, 52b which may inhibit slippage of the filament relative to the anchor 20. However, the filament 50 need not have any protuberances 54a, 54b and still secure the medical article 12 to the anchor 20.

The filament 50 can have a variety of lengths depending upon the particular application of the securement device 10. For example, a securement device 10 configured to retain a medical article 12 that has a large cross-sectional size may comprise a longer filament 50. For use with anchoring catheters and medical tubing, the filament 50 desirably has a length of about 5 inches. However, much longer or short lengths also are possible.

In addition, the intended method of securement of the two portions of the filament 50 to one another may determine the length of the filament 50. A filament 50 which is intended to be secured via a clip or other connector may not be as long as a filament 50 intended to be secured by a complex knot. A complex knot may require additional length to allow the healthcare provider to tie the knot.

In the illustrated embodiment, the filament 50 includes a plurality of protuberances 54a, 54b arranged in series between the ends 52a, 52b of the filament 50. It is contemplated, however, that the filament 50 can be configured to allow a healthcare provider to form the protuberance 54a, 54b in the filament 50 by tying a knot in the filament 50.

The protuberances 54a, 54b can have identical barb-like shapes. Each protuberance 54a, 54b of the filament 50 can have a generally conical shape. Although not illustrated, the protuberances 54a, 54b can take a variety of other shapes, such as for example, hollow conical shapes, arrow shapes, or transverse rib-like shapes. At least a portion of each protuberance 54a, 54b, however, desirably has a diameter which is larger than the diameter of the corresponding aperture 32a, 32b.

As noted above, the filament 50 of the illustrated securement device 10 underlies at least a portion of the structural layer 30, and extends through apertures 32a and 32b. In the illustrated embodiment, the filament has a substantially circular-cross-section outside of the protuberances 54a, 54b, although it will be understood that a wide variety of different shapes may be utilized. The filament 50 also can have various diameter sizes depending upon the required strength of the filament 50. In a particular embodiment, the filament or strand may comprise No. 1 braided silk sutures, although any suitable material may be used.

Advantageously, the material selected for use as a filament 50 is substantially non-extendible about its long axis. The use of such a material inhibits the filament 50 secured about the medical device 12 from loosening once a knot is tied or the filament 50 is otherwise secured in place. A material which is elastically deformable along its long axis may also be used as a filament 50, and the tension in the filament 50 may provide a retaining force which holds the medical article 12 against the anchor 20 if the filament 50 is stretched when the filament 50 is secured about the medical article 12.

In order to inhibit fraying, and to facilitate insertion of the filament 50 through, for example, an aperture 32a, 32b in the medical device 12, the filament 50 may comprise substantially rigid tips. In one embodiment, the ends 52a and 52b of the filament 50 are lacquered. In other embodiments, caps or similar structures covering the ends 52a and 52b of the filament 50 may be utilized. In one embodiment, the cross sectional size of the ends 52a and 52b may be narrower than other portions of the filament 50, such as through the use of a pointed end.

In the illustrated embodiment, the medical article 12 is retained within securement device 12 by tying the filament 50 about the medical article. In other embodiments, however, other methods of securing the medical device 12 in place may be utilized. For example, the two portions of the filament 50 may be secured to one another via a clip, cleat, a cinch, or any other suitable connector.

As can be seen in FIG. 5, in the illustrated embodiment of the securement device 10, the portion of the filament 50 extending between the apertures 32a and 32b is positioned underneath at least a portion of the structural layer 30 and above at least a portion of the adhesive layer 40. In such an embodiment, movement of the filament 50 relative to the anchor 20 may be inhibited, such as by friction between the adjacent layers or via adhesion.

With reference to FIG. 5, the anchor 20 additionally comprises a receptacle for receiving a portion of the filament 50. In the illustrated embodiment, this receptacle takes the form of a longitudinal groove 37 that extends from the aperture 32a to the aperture 32b. In the illustrated embodiment, it can be seen that the filament 50 is positioned within a groove 37 in the underside of the structural layer 30. Although the receptacle takes the form of a groove in the described preferred embodiment of the present invention, those skilled in the art will recognize that receptacles of other forms are also possible.

Additionally, the groove 37 may include an adhesive or a surface treatment which is applied to the inner surface of the groove 37 to further increase the friction between the anchor 20 and the filament 50. Suitable surface treatments include those which increase the "grip" provided by the groove walls, for example by creating a high friction surface within the groove. Examples of such treatments include, without limitation, corona treating, chemical treating, scoring, and adhesive treating. The surface treatment can also be molded into the groove surface (e.g., ridges).

Appropriate adhesive treatments are those which provide permanent bonding between the anchor 20 and the filament 50. The adhesive may be disposed upon the groove 37 (or other receptacle of the anchor 20) by various means, including being applied to the surface from below after the groove 37 is formed, spraying the adhesive into the groove 37, and injecting the adhesive into the groove 37 from above through a hole, such as the aperture 32a, 32b that extends through the top of the anchor 20 of the securement device 10.

Although the filament 50 is illustrated as having a cross-sectional size which is comparable in size to the thickness of the structural layer 30, it will be understood that the filament 50 may be thicker or thinner relative to the thickness of the structural layer 30.

It will also be understood that in other embodiments, the underside of the structural layer 30 may not comprise a groove 37. The filament 50 may be positioned against the surface of the structural layer 30 or sandwiched between multiple structural layers 30 with or without one or more grooves. Thus, in certain embodiments, the adhesive layer 40 and/or the friction between layers located on either side of the filament 50 may be sufficient to hold the flexible layer in place.

Figure 6:
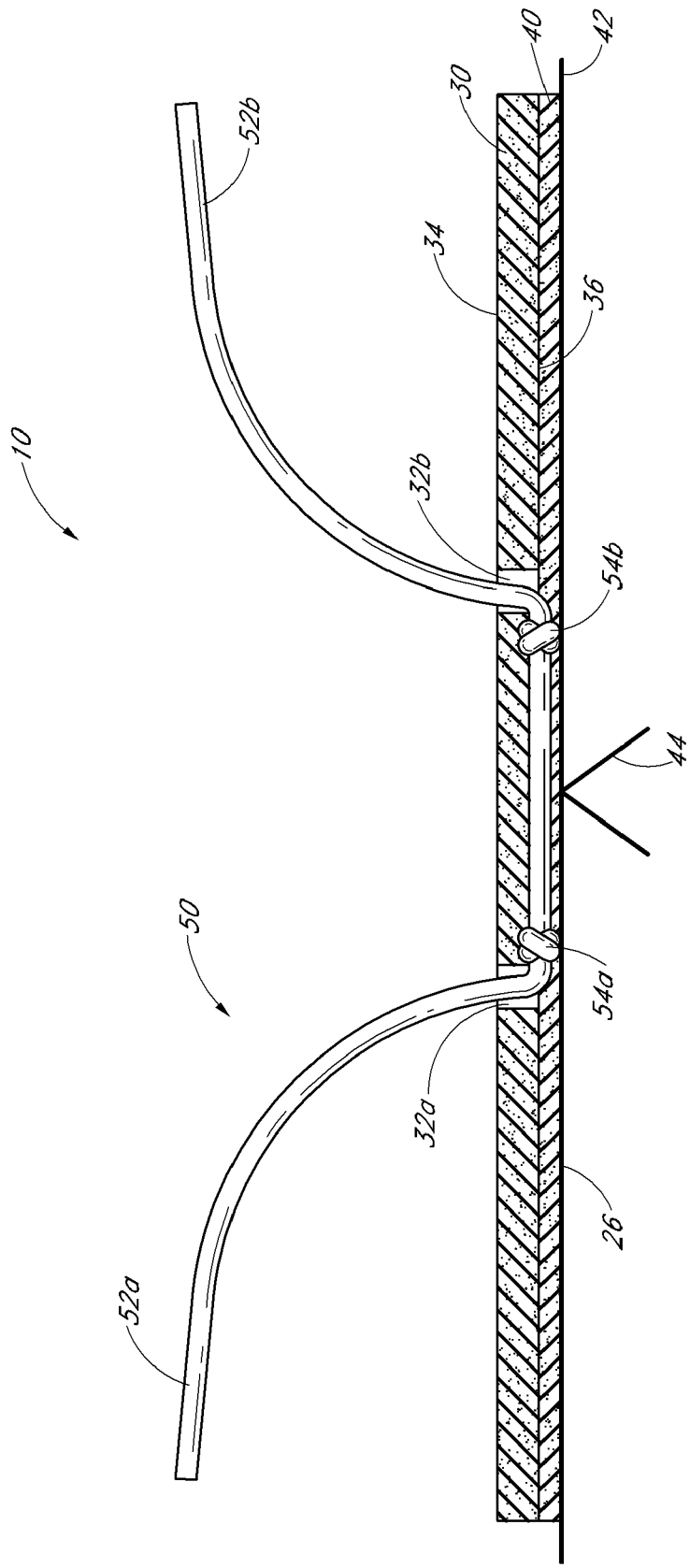
FIG. 6 is a cross sectional view of the securement device of FIG. 3 taken along line 6-6.
Figure 7:
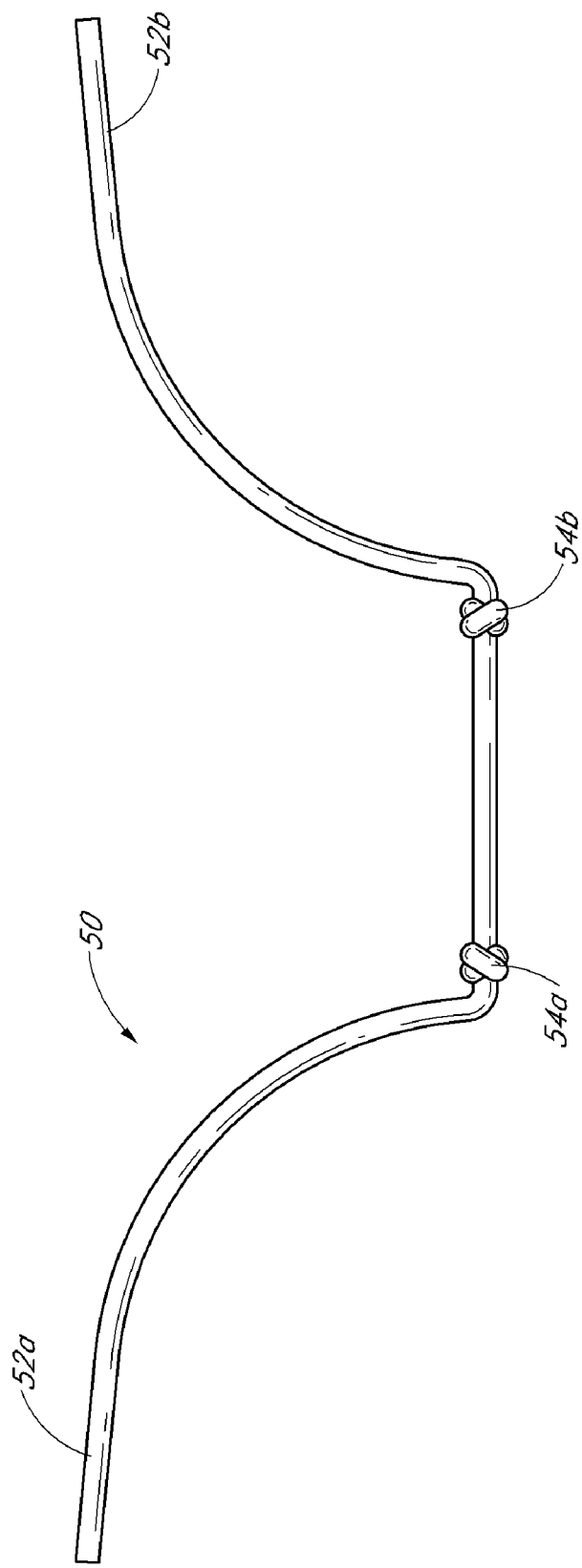
FIG. 7 is a side view of a filament suitable for use with the securement device of FIG. 1.

FIG. 6 is a cross sectional view of the securement device 10 of FIG. 3 taken along line 6-6. FIG. 7 is a side view of the filament 50. As can be seen in FIGS. 6 and 7, the filament 50 may comprise features which inhibit movement of the filament 50 along the long axis of the filament 50 relative to the remainder of the securement device 10. These features may include a portion of the filament 50, such as protuberances 54a, 54b, that have a diameter greater than the diameter of the corresponding aperture 32a, 32b. Each protuberance 54a, 54b may be located along the length of the filament 50 so as to contact the bottom or top surface of the structural layer 30.

In the illustrated embodiment, knots 54a and 54b are formed in the filament 50. In certain embodiments, the knots 54a and 54b may be larger in size than the corresponding aperture 32a, 32b such that the knots 54a, 54b can not be easily pulled through the corresponding aperture 32a, 32b. In other embodiments, the knots may be smaller than the apertures, but a side of the knot's bulbous outer perimeter may catch against the side of the aperture 32a, 32b to inhibit relative movement in at least one direction.

In an embodiment in which the filament 50 is disposed within a groove 37 in the underside of the structural layer, the groove 37 may comprise a wider portion dimensioned to retain the protuberances 54a, 54b. In other embodiments, the protuberances 54a, 54b may be retained between substantially flat adjacent surfaces within the anchor 20.

It will also be understood that features other than protuberances 54a, 54b may be used to inhibit movement along the long axis of the filament 50 or movement of portions of the filament through or beyond the apertures 32a, 32b. For example, the protuberances 54a, 54b may be a wide portion or a radially extending portion or structure secured to the filament 50.

Additional variations on the flexible layer are discussed below.

Medical Article

As noted above, a wide variety of medical devices 12 may be retained via securement device 10. The filament 50 may conform to the shape of any medical device 12 retained between the filament 50 and the anchor 20, although certain medical devices may be further adapted to be retained by the filament 50.

In certain embodiments, the medical device 12 may comprise a flat base portion such that the contact area between the medical device 12 and the anchor 20 is increased. The increased area may provide additional friction and inhibit motion of the medical device in lateral or longitudinal directions relative to the anchor 20. Friction may also be increased if the portion of the medical device 12 in contact with the anchor 20 has a rough surface, or comprises other surface features configured to interact with the anchor 20 so as to inhibit lateral and/or longitudinal movement when the medical device 12 is secured against the anchor 20.

In other embodiments, the medical device 12 may comprise one or more apertures, wherein the apertures are configured to receive a portion of the filament 50. In certain embodiments, the filament 50 passes through at least one aperture in the medical article 12 and the two portions of the filament 50 are secured to one another via a knot or connector. In other embodiments, the filament 50 may be secured to the medical article 12 via such an aperture. In certain embodiments, the apertures may comprise radiused edges, so as to avoid sharp corners which could fray or cause wear on the filament over time.

In other embodiments, the medical device may comprise a circumferential groove configured to receive a portion of the filament. In a particular embodiment, a groove may extend about all or a portion of the medical article 12, and the filament 50 may lie at least partially within the groove when the filament 50 is secured about the medical article 12. Such a configuration may provide additional inhibition against longitudinal movement of the medical article 12 relative to anchor 20.

In addition, it will be understood that the features discussed above are merely examples of a wide variety of other features which may be used to facilitate retention of a medical article 12 via securement device 10.

Operation

In one embodiment, operation of the securement device may proceed as follows. The securement device 10 may first be secured to a portion of a patient's skin before securing the medical article 12 to the receiving space 21. If necessary, the securement site may be cleaned or otherwise prepared by the healthcare provider. The liner 42 is first removed from the anchor 20, exposing the adhesive layer 40 on the underside of the securement device 10. As noted above, this may be done via the use of pull tabs 44 which facilitate removal of the liner 42. The securement device may then be affixed to the skin of the patient, and in certain embodiments, notches or other features of the anchor 20 may be used to facilitate placement or alignment of the securement device 10 by the healthcare provider.

Once the securement device 10 has been affixed to the skin of the patient, the medical article 12 to be retained may be placed on the anchor 20, and oriented relative to the securement device 10. The medical article is preferably positioned such that it is disposed between the apertures 32a and 32b. A central axis of the medical article 12 may be oriented orthogonal to a latitudinal axis extending between the apertures 32a and 32b.

The filament 50 may then be used to secure the medical article 12 in place relative to the securement device 10. In the illustrated embodiment, this may be done by taking the two ends of the filament 50 and using them to tie a knot such that the filament 50 encompasses the medical article 12 and is pulled tight against the medical article 12.

In embodiments in which the structural layer 30 comprises a compressible material, the medical article 12 may be pressed against the structural layer 30 such that the material is deformed in a compressed state when the filament 50 is secured over the medical article 12. The restoring force exerted by the compressed material will push the medical article 12 upward against the overlying portion of the filament 50, holding the medical article 12 tightly against the filament 50.

Additional Embodiments

Figure 8:
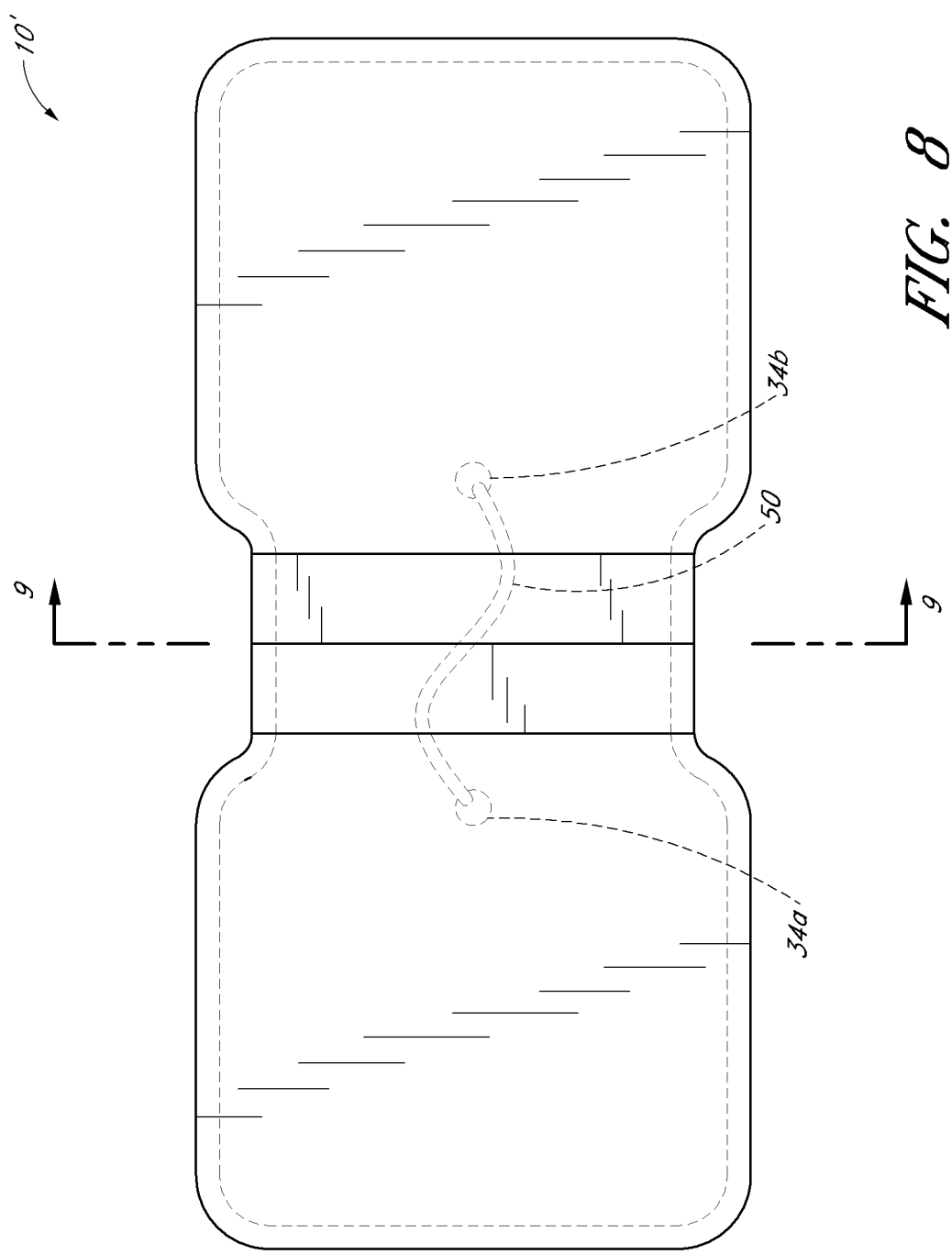
FIG. 8 is a bottom plan view of an alternate embodiment of a securement device wherein the filament extends along an S-shaped path between apertures in the anchor pad.
Figure 9:
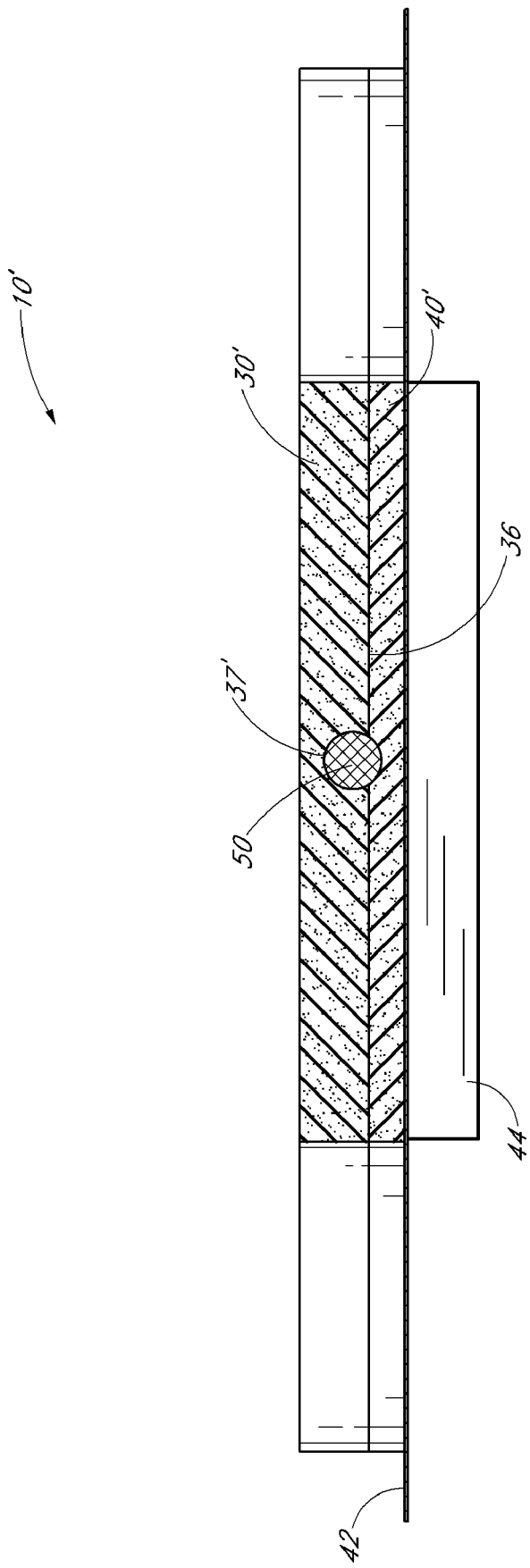
FIG. 9 is a cross sectional view of the securement device of FIG. 8 taken along line 9-9.

As noted above, each of the components of the securement device 10 may be modified. FIGS. 8 and 9 illustrate an alternate embodiment of a securement device 10', which is similar in many aspects to securement device 10 of FIGS. 1-7.

FIG. 8 is a bottom plan view of the securement device 10'. It can be seen that the securement device 10' differs from the securement device 10 of FIGS. 1-7 in that the filament 50' extends between apertures 32a and 32b along a curved groove 37'. The groove 37' follows a laterally curved path from one aperture 32a to the other aperture 32b. Even though the ends of the groove 37' are perpendicular to the longitudinal axis, the groove 37' is longitudinally displaced to one side and then back to the center as it passes through the anchor 20. In the illustrated embodiment, the groove 37' has a serpentine shape.

This serpentine curve in the groove 37' increases the friction which is applied to the outer surface of the filament 50, as will be discussed below. Although the illustrated groove 37' curves to one side and then back in a serpentine shape, those skilled in the art will understand that other curved paths will serve a similar purpose. For example, an S-shaped curve can also be used in practicing the present invention. In the S-shaped curve, the ends of the groove 37' are not aligned longitudinally with one another, and the groove 37' curves first in one direction and then the other in passing through the anchor 20. Another example of a possible groove 37' design is a C-shaped curve. In the C-shaped curve, the path of the groove 37' is not perpendicular to the ends of the groove 37', and the groove 37' curves in only one direction as it passes through the anchor 20. Various other shapes for grooves 37' will be apparent from the above to those skilled in the art.

In FIG. 9, it can also be seen that the groove 37' in the underside of structural layer 30' extends more than 180° around the filament 50, increasing the surface area of the groove 37' in contact with the filament 50, which may provide additional inhibition against movement of the filament 50 relative to the remainder of the securement device 10'. In another embodiment, securement devices may include structures overlying the anchor 20 and configured to contact and support medical devices.

As can be seen in FIG. 10, securement device 10" comprises an anchor 20 which is similar in structure and shape to the anchor 20 of FIG. 1, as well as a filament 50 which is similar in structure and shape to the filament 50 of FIG. 1. However, securement device 10" differs from the securement device 10 of FIG. 1 in that securement device 10" comprises an overlying member 60 connected to and located above the anchor 20 and located between apertures 32a and 32b.

In the illustrated embodiment, overlying member 60 is secured to the anchor 20 via an adhesive, although other methods of securing the overlying member 60 to the anchor 20 may be utilized. As noted above, the use of an anchor 20 having a structural layer with a roughened upper surface 34 may strengthen an adhesive joint between the two components.

It can be seen that overlying member 60 comprises a contoured upper surface 62 configured to interact with the medical device 12 to inhibit movement of the medical device 12 relative to securement system 10" in at least one direction. In other embodiments, however, the upper surface of the overlying member may not be contoured, or may be deformable by the medical article. For example, the upper surface of the overlying member may be overmolded with an elastomeric material, which will be deformable by the medical article when the medical article is held against the overlying member.

It can also be seen in FIG. 10 that the overlying member 60 comprises notches 64a and 64b extending transversely along the lateral sides of the overlying member 60 and aligned with apertures 32a and 32b. These notches 64a and 64b may be configured to receive a portion of the filament 50 when the filament 50 is pulled tight over a medical article 12. When the notches 64a and 64b are located close to apertures 32a and 32b, the acuteness of the angle between the flexible layer 50 and the anchor pad may be decreased, reducing the stress on the interior sides of the apertures 32a and 32b.

In other embodiments, rather than notches or groves, the overlying member may comprise apertures extending therethrough. In particular embodiments, these apertures may overlie the apertures 32a and 32b in the structural layer 30, and may extend in a substantially transverse direction.

In certain embodiments, the filament 50 may be located between overlying member 60 and anchor 20, rather than between structural layer 30 and adhesive layer 40 of anchor 20. In such an embodiment, movement of the filament 50 relative to securement device 10' may be inhibited by friction or by an adhesive securing the overlying member 60 to anchor 20. In alternate embodiments, the filament 50 may be disposed within a groove in the base of the overlying member 60, or within a groove in the upper surface of structural layer 30 of anchor 20.

In certain embodiments, as noted above, the securement structure may comprise a compressible portion. In an embodiment comprising an overlying member 60, either or both of the overlying member 60 or the structural layer 30 may comprise a compressible portion. As noted above, in an embodiment in which the overlying member 601 comprises a deformable material, the medical article 12 may be pressed against an upper surface of the overlying member 60 so as to define a matching contour in the overlying member. The restoring force exerted by the deformed material may hold the medical article 12.

In some embodiments, multiple filaments 50 may be used, and may extend either through the same pair of apertures, or through distinct pairs of apertures. The filament 50 may comprise a substantially flat band, rather than a strand having a substantially circular cross-section or similar, and the apertures may be comprise flat edges on at least the interior side of the apertures. Such a configuration may reduce the likelihood of tearing, as a wide band is pulled against the edge of an aperture, rather than a strand which may be very narrow.

In some embodiment, multiple components of the securement device may be formed as a unitary structure. For example, the filament 50 may be formed as a unitary structure with the anchor 20, such that a filament portion extends from two or more locations on the anchor. In such embodiments, there is no need to form apertures through the anchor for the purpose of passing a portion of the filament therethrough. Similarly, there is no need for the anchor to comprise multiple layers having a portion of the filament disposed therebetween. An adhesive may be applied to the underside of such a unitary structure. In addition, the unitary structure may also comprise a shaped or deformable upper portion similar to overlying member 60.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above, but should be determined only by a fair reading of the claims that follow.

What is claimed is:

1. A device for securing a medical article to the body of a patient, comprising:
   an adhesive layer configured to contact the skin of a patient;
   a structural layer overlying the adhesive layer, said structural layer comprising at least one aperture extending therethrough, a receptacle, and a receiving space, wherein at least a portion of said receptacle is disposed below said receiving space; and
   a filament comprising two free ends and at least one protuberance disposed therebetween, said filament extending underneath a portion of said structural layer and through said aperture and said receptacle, said two free ends being movable from an unsecured position to a secured position, at least a portion of a medical article being secured against said receiving space at least when said two free ends are in said secured position, at least a portion of said protuberance being disposed within said receptacle at least when said two free ends are in said unsecured position so as to inhibit motion of said filament relative to said structural layer in a direction parallel to said filament.

2. The device of claim 1, wherein at least a portion of the structural layer comprises a tear-resistant material.

3. The device of claim 1, wherein at least a portion of the structural layer comprises a compressible material.

4. The device of claim 1, wherein the structural layer comprises at least two apertures extending therethrough.

5. The device of claim 4, wherein the filament extends beneath the structural layer and between the at least two apertures.

6. The device of claim 5, wherein the filament is disposed at least partially within a groove in the structural layer.

7. The device of claim 4, wherein at least a portion of the structural layer located between the at least two apertures comprises a compressible material.

8. The device of claim 1, wherein at least a portion of the structural layer adjacent the at least one aperture comprises a tear-resistant layer.

9. The device of claim 1, wherein at least a portion of the structural layer underlies at least a portion of the filament.

10. The device of claim 1, wherein the protuberance comprises a knot formed in the filament.

11. The device of claim 1, additionally comprising a member overlying the structural layer, wherein said overlying member is configured to contact and support the medical article retained therein.

12. The device of claim 11, wherein the overlying member comprises a contoured upper surface shaped to receive the medical article thereon.

13. The device of claim 1, wherein the filament is configured to be secured about the medical article without the use of adhesive.

14. A securement device for retaining a medical article therein, comprising:
   a base portion configured to be secured to the skin of a patient, the base portion comprising a receiving space and a receptacle disposed below the receiving space; and
   a filament comprising two free ends and at least one protuberance disposed therebetween, said filament extending underneath at least a receiving portion of the base portion, said two free ends being movable from an unsecured position to a secured position, at least a portion of a medical article being secured within said receiving space at least when said two free ends are in said secured position, at least a portion of the protuberance being disposed within the receptacle at least when said two free ends are in said unsecured position so as to inhibit motion of the filament relative to the base layer in a direction parallel to the filament, wherein the receiving portion is configured to contact the medical article retained therein, and wherein said receiving portion comprises a compressible material.

15. The device of claim 14, wherein the filament extends through two apertures in the base portion located on either side of the receiving portion.

16. The device of claim 14, wherein the base portion comprises an anchor, the anchor comprising:
    an adhesive layer configured to contact the skin of a patient; and
    a structural layer overlying the adhesive layer.

17. The device of claim 16, wherein the receiving portion comprises a member overlying the structural layer, and wherein the overlying member is configured to contact and support the medical article.

18. The device of claim 17, wherein the filament extends underneath at least a portion of the overlying member.

19. The device of claim 17, wherein the overlying member comprises a compressible material.

20. A device for securing a medical article in place, comprising:
    an adhesive layer;
    a structural layer overlying the adhesive layer, the structural layer comprising a receiving space and a receptacle disposed below the receiving space;
    at least two apertures extending through the structural layer, wherein a portion of the structural layer located between said at least two apertures comprises a compressible material, and wherein at least a portion of the structural layer located adjacent said at least two apertures comprises a tear-resistant material; and
    a filament comprising two free ends and at least one protuberance disposed therebetween, said filament extending underneath at least a portion of the structural layer and between the at least two apertures, said two free ends being movable from an unsecured position to a secured position, at least a portion of a medical article being secured within said receiving space at least when said two free ends are in said secured position, at least a portion of the protuberance being disposed within the receptacle at least when said two free ends are in said unsecured position so as to inhibit motion of the filament relative to the structural layer in a direction parallel to the filament, wherein said filament is configured to be secured about the medical article without the use of adhesive.

21. The device of claim 20, wherein the filament is disposed within a groove on the underside of the structural layer.

22. The device of claim 21, wherein the groove extends along a non-linear path between the at least two apertures.

23. An anchoring system for securing a portion of a medical article to a body of a patient, said anchoring system comprising:
    an anchor having two apertures and a receiving space therebetween, the two apertures being disposed below the receiving space and spaced from each other so as to receive at least a portion of the medical article on said receiving space; and
    at least one filament passing through the two apertures and having two ends, the two ends being movable from an unsecured position to a secured position, at least a portion of a medical article being secured within said receiving space at least when said two ends are in said secured position, the filament including a first set of protuberances, said first set of protuberances being positioned between said two ends of said filament and below said anchor at least when said two ends are in said unsecured position, at least a portion of the filament being sized and shaped to pass through the two apertures, and each protuberance being sized and shaped to inhibit movement of the filament through one of the apertures in a first direction.

24. The system of claim 23, wherein the filament includes a second set of protuberances, each protuberance of the second set of protuberances being sized and shaped to inhibit movement of the filament through one of the apertures in a direction opposite to the first direction.

25. The system of claim 23 further comprising an adhesive layer and a structural layer overlying the adhesive layer.

26. The system of claim 25, wherein the at least one filament is disposed within a groove on the underside of the structural layer.

27. The device of claim 21, wherein the groove is disposed below said receiving space.

28. The device of claim 6, wherein the groove is disposed below said receiving space.

* * * * *